United States Patent [19]

Simon-Bierenbaum et al.

[11] 4,424,396

[45] Jan. 3, 1984

[54] PROCESS FOR THE PREPARATION SUBSTITUTED ANILINO ACIDS

[75] Inventors: R. Simon-Bierenbaum, Buffalo, N.Y.; Ernest W. Ertley, Mission Viejo; Frederick J. Goetz, Santa Ana, both of, CA; David Y. Tang, Tonawanda, N.Y.

[73] Assignee: Occidental Chemical Corporation, Niagara Falls, N.Y.

[21] Appl. No.: 400,219

[22] Filed: Jul. 21, 1982

[51] Int. Cl.³ .............................................. C07C 99/00
[52] U.S. Cl. .................................... 562/456; 562/433
[58] Field of Search ..................... 564/407; 560/43; 562/456, 433

[56] References Cited

U.S. PATENT DOCUMENTS

| | | | |
|---|---|---|---|
| 3,484,487 | 12/1969 | Dix | 564/407 |
| 4,096,185 | 6/1978 | Seiwell | 564/407 |
| 4,226,802 | 10/1980 | Anderson et al. | 260/465 D |
| 4,243,819 | 1/1981 | Henrick et al. | 560/43 |

OTHER PUBLICATIONS

Zahn et al., Biochem Z, vol. 325, pp. 333-338, (1954).

Primary Examiner—James H. Reamer
Attorney, Agent, or Firm—James F. Tao; Arthur S. Cookfair

[57] ABSTRACT

Anilino acids of the formula

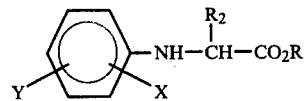

wherein R is H or a metal cation; $R_2$ is hydrogen or lower alkyl of 1 to 5 carbon atoms, lower alkenyl of 2 to 5 carbon atoms, lower haloalkyl of 1-4 carbon atoms, lower haloalkenyl of 2 to 4 carbon atoms, or lower cycloalkyl of 3 to 4 carbon atoms, Y is hydrogen, chloro, methyl group, or trifluoromethyl group, and X is hydrogen, chloro, or fluoro are prepared by reaction of an aryl halide of the formula

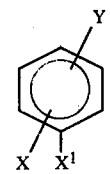

where $X^1$ is chloro or fluoro and X and Y are as defined above with the proviso that when $X^1$ is chloro, X is hydrogen or chloro, and when X and Y are both chloro, $X^1$ is fluoro with an α-amino acid of the formula

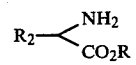

where R and $R_2$ are as defined above.

30 Claims, No Drawings

PROCESS FOR THE PREPARATION SUBSTITUTED ANILINO ACIDS

BACKGROUND OF THE INVENTION

Substituted anilino acids of the formula

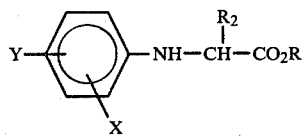

where R is H or a metal cation; $R_2$ is H or alkyl of 1 to 5 carbon atoms, lower alkenyl of 2 to 5 carbon atoms, lower haloalkyl of 1–4 carbon atoms, lower haloalkenyl of 2 to 4 carbon atoms, or lower cycloalkyl of 3 or 4 carbon atoms, Y is hydrogen, chloro, methyl group, or trifluoromethyl group, and X is hydrogen, chloro, or fluoro; are prepared by the reaction of a substituted aryl halide with an α-amino acid.

The anilino acids which may be prepared in accordance with this invention are useful as intermediates in the synthesis of various pesticidal compounds, particularly pesticidal compounds of the synthetic pyrethroid type such as those set forth in U.S. Pat. Nos. 4,260,633; 4,226,802; and 4,161,537.

It is shown in the chemical literature that a highly activated aryl halide, in particular, 2,4-dinitro-5-chlorofluorobenzene will react with glycine to synthesize 2-(2,4-dinitro-5-chlorphenylamino)propionic acid (Zahn et al.; Bhiochem. Z. 325, 333 (1954). However, the prior art has not shown the reaction of amino acids with aryl halides that lack the high activation effect of nitro groups on the aromatic nucleus. As a result the development of methods for the preparation of other substituted anilino acids such as trifluoromethylphenylamino-alkanoic acids has followed a substantially different route of synthesis.

The preparation of certain aryl amines such as anilines and substituted anilines by amination of an aryl halide is known. U.S. Pat. No. 4,096,185, to Linda P. Seiwell, discloses the preparation of p-aminobenzotrifluoride (also referred to as p-trifluoromethylaniline) by reaction of p-chlorobenzotrifluoride with ammonia in the presence of a copper halide catalyst. U.S. Pat. No. 3,484,487 to James S. Dix discloses the preparation of aryl amines, such as N,N-dimethylaniline by reaction of an aryl halide with an animating agent such as ammonia or an alkylamine in the presence of a copper chloride catalyst and a polar organic solvent such as sulfolane. Compounds of the type shown in formula I, above, and the use thereof in the synthesis of various N-substituted esters are disclosed in U.S. Pat. No. 4,243,819 to Henvick and Garcia. Thus, for example, it is shown that the m-phenoxybenzyl ester of N-(trifluoromethylphenyl) valines may be prepared by the reaction of trifluoromethylaniline with m-phenoxybenzyl α-bromoisovalerate.

Typically, the prior art methods for the preparation of anilino acids of the type characterized by the formula (I) above, have involved the preparation of an appropriately substituted aniline, for example by the methods disclosed in the preceeding paragraph, and reaction of the aniline with an appropriately substituted alkanoic acid. Thus, for example, it is known from U.S. Pat. No. 4,260,633 to Anderson et al. to prepare 2-(4-trifluoromethylphenylamino)-3-methylbutanoic acid by reaction of 2-bromo-3-methylbutanoic acid with 4-trifluoromethylaniline. The product may then be chlorinated by reaction with N-chlorosuccinimide to prepare 2-(2-chloro-4-trifluoromethyl-phenylamino)-3-methylbutanoic acid, a particularly useful intermediate for the preparation of fluvalinate pesticide.

U.S. Pat. No. 4,226,802 to Anderson et al., discloses the synthesis of 2-(4-trifluoromethylphenylamino)-3-methylbutanoic acid and alkyl esters thereof by reacting p-trifluoromethylphenylamine with the bisulfite addition product of isobutyraldehyde, followed by reaction with an alkali metal cyanide and treatment of the resulting nitrile with a strong acid and an alcohol. The resulting ester may then be converted to the acid.

Thus, the prior art synthesis of such substituted anilino acids have typically involved multi-step procedures that are complex and uneconomical. It has now been found, in accordance with this invention, that substituted anilino acids of the type shown by formula I, above may be directly and economically prepared by the reaction of a suitable aryl halide with an α-amino acid.

SUMMARY OF THE INVENTION

This invention provides a novel process for the preparation of anilino acids of the formula

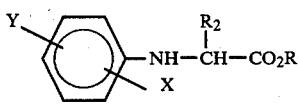 I wherein R is H or a metal cation; $R_2$ is H or alkyl of 1 to 5 carbon atoms, lower alkenyl of 2 to 5 carbon atoms, lower haloalkyl of 1–4 carbon atoms, lower haloalkenyl of 2 to 4 carbon atoms, or lower cycloalkyl of 3 or 4 carbon atoms, Y is hydrogen, chloro, methyl group or trifluoromethyl group, and X is hydrogen chloro, or fluoro, which comprises reacting an aryl halide of the formula

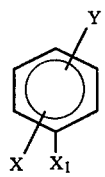 II wherein $X^1$ is chloro or fluoro and X and Y are as defined above with the proviso that when $X^1$ is chloro, X is hydrogen or chloro, and when X and Y are both chloro, Y is fluoro, with an α-amino of the formula

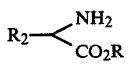 III wherein R and $R_2$ are as defined above.

The compounds prepared in accordance with this invention (formula I) are characterized by a chiral center at the 2-carbon and thus may be prepared as either R or S enantiomers or as a racemic mixture thereof depending on the configuration of the α-amino acid reactant the reaction conditions.

Suitable aryl halides that may be employed are mono and dehalobenzenes, mono and dihalotoluenes and mono and dihalobenzotrifluorides where the halo is fluoro or chloro, including, for example, monochlorobenzene; o-dichlorobenzene; monofluorobenzene; o-difluorobenzene; o-chlorofluorobenzene; 3-chlorotoluene; 3-fluorotoluene; 4-chlorotoluene; 4-fluorotoluene; 3,4-dichlorotoluene; 3,4-difluorotoluene; 3-chloro-4-fluorotoluene; 4-chloro-3-fluorotoluene; 3-chlorobenzotrifluoride; 3-fluorobenzotrifluoride; 4-chlorobenzotrifluoride; 4-fluorobenzotrifluoride; 3,4-dichlorobenzotrifluoride; 3,4-difluorobenzotrifluoride; and 3-chloro-f-fluorobenzotrifluoride; 4-chloro-3-fluorobenzotrifluoride; 5-chloro-2-fluorobenzotrifluoride; 2-chloro-5-fluorobenzotrifluoride; 2,5-dichloro-4-fluorobenzotrifluoride; and the like.

Suitable amino acids include, for example, glycine alanine, leucine, isoleucine, phenylalanine, and the like. The amino acid reactant is preferably employed as a salt thereof, preferably an alkali metal salt, especially a potassium salt. The amino acid salt may be added initially to the reaction mixture, or may be formed in-situ in the reaction mixture. Thus, for example, an alkali metal salt of the amino acid may be added or may be formed in-situ by the addition of the amino acid and an alkali metal compound, wuch as an alkali metal carbonate. It is preferred to carry out the reaction in the presence of an excess of a base, such as an alkali metal carbonate, in a stoichiometric amount greater than that required for the formation of the salt of the amino acid. Preferably a stoichiometric excess of at least about one is employed to neutralize acid generated in the course of the reaction and to above protonation of the amino acid salt and consequent inhibition of the reaction.

The process of this invention is preferably carried out in the presence of a solvent. The reaction may be run neat, but is generally less efficient under such conditions. Preferred solvents are dipolar, aprotic solvents such as sulfolane, dimethyl sulfoxide, dimethyl formamide, N-methyl-2-pyrrolidone and the like.

The reaction conditions may vary considerably. It is preferred to utilize atmospheric or super-atmospheric pressures. Sub-atmospheric pressures may be employed, but are not recommended. The temperature of the reaction may vary considerably, but is typically in the range of about 80° to about 190° C. and most preferably in the range of about 90° C. to about 160° C. Depending on the reactants employed, a catalyst, such as a phase transfer catalyst or a transition metal catalyst, may be employed to enhance the efficiency of the reaction. Typical transition metal catalysts include, for example, organometallic complexes ($M^o$) of transition metals and/or transition metal salts. Preferred catalysts are the Cu (I) and Cu (II) salts, such as copper halides. Typical phase transfer catalysts include for exampe, tetraalkyl ammonium halides, 18-crown-5-ether, and the like.

The use of a transition metal catalyst may depend on the aryl halide reactant employed. When the reactive aryl halide site is fluoro-, for example, when the reactant is p-fluorobenzotrifluoride, the reaction will generally proceed with ease, and the presence of a transition metal catalyst will provide little or no advantage. However, when the reactive site is chloro-, for example, when the reactant is p-chlorobenzotrifluoride, a transition metal catalyst may be advantageously employed. However, in some instances, when the aryl halide is a substituted dichlorobenzene, the improvement in reactivity achieved with the use of a transition metal catalyst, may be accompanied by some loss in selectivity. Thus, for example, when 3,4-dichlorobenzotrifluoride is reacted with valine, the reaction occurs preferentially at the chlorine site para- to the trifluoromethyl group, the major product being 2-(2-chloro-4-trifluoromethylphenylamino)-3-methylbutanoic acid. Generaly a minor reaction will occur at the meta-chloro position to produce a small amount of 2-(2-chloro-5-trifluoromethylphenylamine)-3-methylbutanoic acid as an undesired by-product. The addition of a transition metal catalyst to the reaction will result in substantial improvements in total yield accompanied by a loss in selectively evidenced by an increase in the percentage of metasubstituted by-product, 2-(2-chloro-5-trifluoromethylphenylamine)-3-methylbutanoic acid.

The greater reactivity of the nuclear fluorine site may be used to particular advantage in the synthesis of the intermediate 2-(2-chloro-4-trifluoromethylphenylamino)-3-methylbutanoic acid by the reaction of a carboxylate salt of valine, such as a potassium salt of valine with 3-chloro-4-fluorobenzotrifluoride. The product 2-(2-chloro-4-trifluoromethylphenylamino)-3-methylbutanoic acid is particularly useful as an intermediate for the further preparation of the pesticide fluvalinate. It has been found that the use of 3-chloro-4-fluorobenzotrifluoride in the forementioned synthesis is especially advantageous in that reaction occurs preferentially at the fluorine site to provide a high yield of the desired product with little or no formation of unwanted by-products. The product compound, prepared in a single step reaction is characterized by the presence of a nuclear chlorine atom at the α-position of the phenyl moiety. Processes of the prior art require additional steps to complete the synthesis of this compound.

The process of the invention is particularly useful in the preparation of isovaleric acid derivatives which, in turn, are useful as intermediates for the preparation of various agricultural chemicals, expecially synthetic pyrethroid insecticides. Accordingly, in a preferred embodiment, the present invention is directed to a process for the preparation of isovaleric acid derivatives characterized by the formula

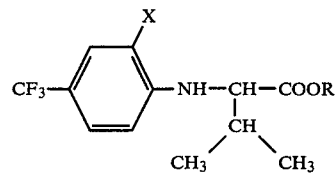

IV

Wherein X is hydrogen, chloro, or fluoro, and R is hydrogen or a metal cation. These isovaleric acid derivatives may be esterified under moderate conditions with an alcohol of the formula

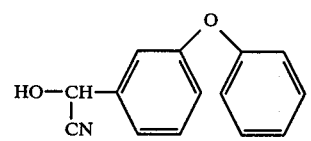

V to synthesize a pyrethroid of the formula

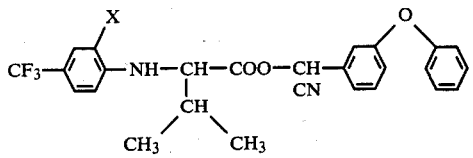

The esterification reaction may be carried out at relatively low temperature, such as 0° to about 25° Celsius, preferably in the presence of a solvent such as hexamethylphosphoric triamide, tetrahydrofuran, dimethylformamide, dimethylsulfoxide and the like.

The esters (VI) thus prepared is a diastereomer wherein the acid and alcohol moiety each possess chiral centers and thus each may be in either the R or S configuration. However, it is known that the various possible diastereomeric pairs differ substantially in pesticidal activity, the most highly active pesticidal activity being exhibited by esters wherein the acid portion is in the R configuration and the alcohol portion is in the S configuration or a mixture of the S configuration and the R configuration. Thus, it is especially advantageous to prepare isovaleric acid derivatives of the formula IV, above, as an optically pure or optically enriched R-enantiomer.

It has not been found that the R-enantiomer of 2-(2-chloro-4-fluoromethylphenylamino)-3-methylbutanoic acid may be prepared in relatively high optical and chemical purity by reacting 3-chloro-4-fluorobenzotrifluoride with potassium R-valinate in the presence of 40 to 75 mole percent of potassium carbonate in excess of the stoichiometric amount required to form potassium R-valinate, in a dipolar aprotic solvent at a temperature of about 100° to about 160° Celsius, most preferably about 110° to about 150° Celsius. By such procedure R-2-(2-chloro-4-trifluoromethylphenylamino)-3-methylbutanoic acid may be prepared in greater than about 80% optical and chemical purity, and products having an optical and chemical purity of 99% or higher have been achieved.

Typical isovaloric acids (IV), prepared in accordance with the process of this invention and pesticidal esters (VI) that may be prepared therefrom are as follows:

| Isovaleric Acid (IV) | Alcohol (V) | Pesticidal Ester (VI) |
|---|---|---|

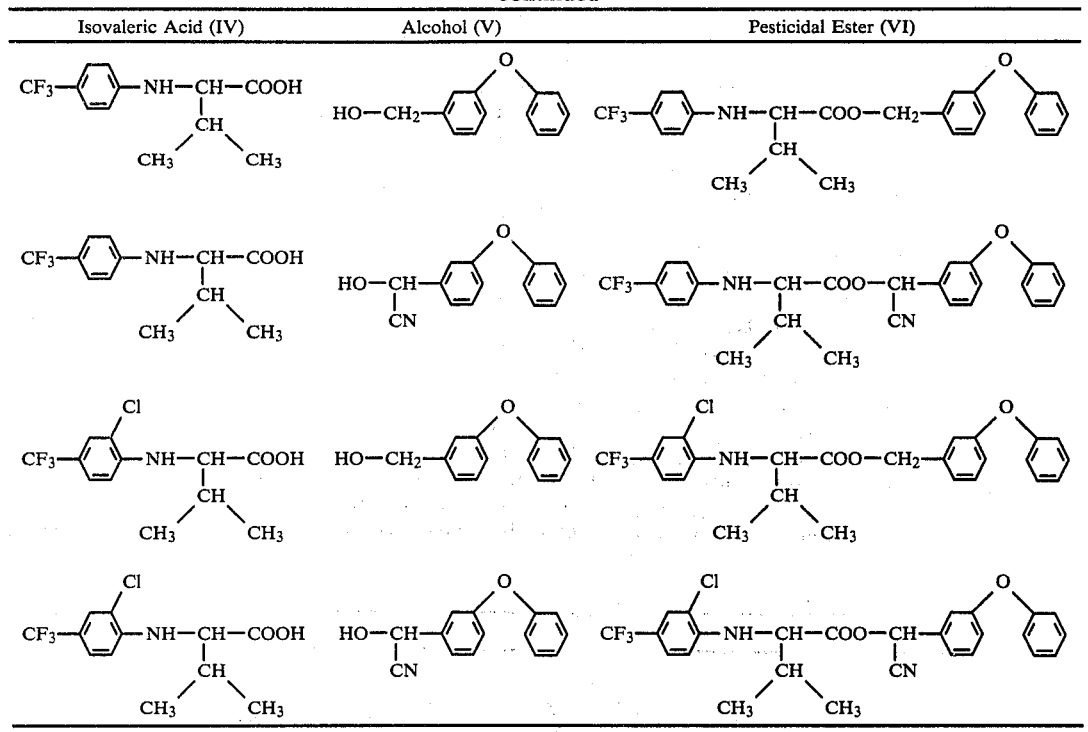

The following specific examples are provided to further illustrate this invention and the manner in which it may be carried out. It will be understood, however, that the specific details given in the examples have been chosen for the purpose of illustration and are not to be construed as a limitation on the invention. In the examples, unless otherwise indicated, all parts and percentages are by weight and all temperature are in degrees Celsius, and reactants and products having chiral centers are employed as racemic mixtures.

EXAMPLE I

A mixture of 10 parts of 3,4-dichlorobenzotrifluoride, 23 parts of potassium valinate and 60 parts of sulfolane was heated and maintained at about 160° C. for about 48 hours, with mixing. The mixture was then cooled to room temperature, diluted with water, acidified with hydrochloric acid to a pH of 1.0. The aqueous layer was extracted with diethyl ether. The ether layers were washed with water, then dried and concentrated by evaporation to yield 10.4 parts of 2-(2-chloro-4-trifluoromethylphenylamino)-3-methylbutanoic acid (85% purity); a yield of about 75% based on the dichlorobenzotrifluoride starting material.

EXAMPLE II

A mixture of 10 parts of 3-chloro-4-fluorobenzotrifluoride, 10 parts of potassium valinate and 50 parts of sulfolane was heated and maintained at about 125° C. for about 17 hours, with mixing. The mixture was then cooled to room temperature, diluted with water and acidified with hydrochloric acid to a pH of 1.0. The aqueous layer was extracted with diethyl ether. The ether layers were washed with water, then dried and concentrated by evaporation to yield 9.6 parts of 2-(2-chloro-4-trifluoromethylphenylamino)-3-methylbutanoic acid (96% purity); a yield of about 65% based on the 3-chloro-4-fluorobenzotrifluoride starting material.

EXAMPLE III

A solution of 20 parts of 3-chloro-4-fluoro-benzotrifluoride, 7.2 parts of R-valine, 8.5 parts of potassium carbonate in 30 parts of m-pyrol, was heated and maintained at about 125° C. for about 16 hours, with mixing. The mixture was then cooled to room temperature, and treated as in Examples 1 and 2 to recover 17.9 parts of 2-(2-chloro-4-trifluoromethylphenylamino)-3-methylbutanoic acid (99% chemical purity and 99% optical purity); a yield of about 98% based on valine starting material.

EXAMPLE IV

The procedure of Example III was repeated except that R-valine was replaced with a racemic mixture of valine. A yield of 17.5 parts of 2-(2-chloro-4-trifluoromethylphenyl-amino)-3methylbutanoic acid (97.7% purity) was obtained.

EXAMPLE V

A reaction mixture of 10 parts of 3,4-difluorobenzotrifluoride, 17 parts of potassium R-valinate, and 60 parts of sulfolane was heated and maintained at about 125° C., with stirring, for about 16 hours. The mixture was then diluted with water, acidified with hydrochloric acid to a pH of 1.0. The aqueous layer was extracted twice with diethyl ether. The ether extracts were combined, washed with water several times, then dried and concentrated by evaporation to yield 13.6 parts of 2-(2-fluoro-4-trifluoromethylphenylamino)-3-methylbutanoic acid; and a yield of about 89.0% based on the difluorobenzotrifluoride starting material.

EXAMPLE VI

A mixture of 30 parts of potassium valinate, 15 parts of p-fluoro-benzotrifluoride, 7 parts of dichlorohexano-18-crown-6 ether catalyst, 10 parts of potassium carbonate and 126 parts of sulfolane was placed in a pressure reactor. The reactor was degassed, placed under an argon atmosphere and sealed. The reaction mixture was then heated and maintained at about 100° C. for about 15 hours. Analysis of the reaction product indicated a 7.0% yield of 2-(4-trifluoromethylphenylamino)-3-methylbutanoic acid based on p-fluorobenzotrifluoride starting material.

EXAMPLE VII

A mixture of 80 parts of p-fluorobenzotrifluoride, 114 parts of valine, 135 parts of potassium carbonate, 65 parts of tetra(n-butyl)ammonium iodide, and 630 parts of sulfolane was placed in a pressure reactor. The reactor was degassed, placed under an argon atmosphere, sealed, and then heated and maintained at about 140° C. for about 18 hours. Analysis of the reaction product indicated 53.0% yield of 2-(4-trifluoromethylphenylamino)-3-methylbutanoic acid, based on p-fluorobenzotrifluoride starting materials.

The fluorochlorobenzotrifluorides are preferred reactants for use in the process of this invention, especially for the synthesis of aniline acids wherein it is desired to provide a chlorine atom on the phenyl moiety. Examples VIII–XI illustrate typical preparation and use of fluorochlorobenzotrifluorides in the process of the invention.

EXAMPLE VIII (A) A mixture of 22.6 parts of 4-chloro-3-nitrobenzotrifluoride, 9.3 parts of potassium fluoride, and 1.4 parts of tetramethylammonium bromide catalyst was heated and maintained at about 165.0° C. for about 9 hours. The reaction mixture was then cooled to room temperature and filtered. The filtrate was distilled under reduced pressure to yield 161 parts of 4-fluoro-3-nitrobenzotrifluoride.

(B) Nine parts of the 4-fluoro-3-nitrobenzotrifluoride of Example I, and six parts of phosphorous pentachloride were sealed tightly under a nitrogen atmosphere in a tubular reactor. The sealed reactor was heated in an oil bath for about two hours at 170°–180° C. The reaction mixture was poured into water and extracted with diethyl ether. The organic layer was dried and distilled at atmospheric pressure to yield 13.6 parts of 3-chloro-4-fluorobenzotrifluoride. The structure was confirmed by gas chromatography—mass spectrum, and by $F^{19}$ and $C^{13}$ NMR analyses.

(C) A mixture of 3.04 parts of 3-chloro-4-flurobenzotrifluoride, 4.5 parts of anhydrous potassium salt of valine, 0.98 parts of tetramethyl-ammonium chloride and 24.0 parts of sulfolane solvent was charged to a reaction vessel, the mixture was heated to 125° C. and maintained thereat for about 16 hours then cooled, diluted with water and acidified to a pH of 1. The aqueous layer was extracted several times with diethyl ether. The ether layer was then washed with copious amounts of water, then dried and concentrated to yield 3.4 parts of 2-(2-chloro-4-trifluoromethylphenyl-amino)-3methylbutanoic acid.

EXAMPLE IX (A) In a continuous process, about 14 parts per hour of 2-fluoro-5-nitrobenzotrifluoride vapors and about 12 parts per hour of chlorine gas were passed simultaneously through a vapor-phase reactor maintained at a temperature of about 320° to 380° C. The vaporized reaction product was condensed and collected. The process was continued until about 20 parts of 2-fluoro-5-nitrobenzotrifluoride and about 17.3 parts of chlorine gas had been passed through the reactor. Analysis of the reaction product indicated 16.7 parts of 5-chloro-2-fluorobenzotrifluoride, a yield of 89%. The structure of the product was confirmed by gas chromatograph—mass spectrum $F^{19}$ and $C^{19}$ nuclear magnetic resonance analysis.

(B) Following the general procedure of Example 8C, 5-chloro-2-fluorobenzotrifluoride is reacted with anhydrous potassium valinate to prepare 2-(4-chloro-2-trifluoromethylphenylamino)-3-methylbutanoic acid.

EXAMPLE X (A) 14.1 parts of 5-fluoro-2-nitrobenzotrifluoride vapors and 12.1 parts of chlorine gas were passed simultaneously, over a one hour period, through a vapor-phase reactor maintained at a temperature of about 320° to 380° C. The vaporized reaction product was condensed and collected. Analysis of the reaction product indicated 12.6 parts of 2-chloro-5-fluorobenzotrifluoride, a yield of 94%. The structure of the product was confirmed by gas chromatography—mass spectrum $F^{19}$ and $C^{13}$ nuclear magnetic resonance analysis.

(B) Following the general procedure of Example 2, 2-chloro-5-fluorobenzotrifluoride is reacted with potassium valinate to prepare 2-(4-chloro-3-trifluoromethylphenylamino)-3-methylbutanoic acid.

EXAMPLE XI (A) About 500 parts of aqueous nitric acid was added slowly, with stirring, to about 400 parts of 3-chloro-4-fluorobenzotrifluoride. The temperature of the reaction mixture was maintained at about 40° C. during the addition, then raised to about 60° C. and maintained thereat for about 5 hours. The reaction mixture was allowed to settle. The aqueous layer was removed and the organic layer washed twice with 500 parts of water, treated several times with a saturated solution of sodium bicarbonate, washed with water again, dried over anhydrous magnesium sulfate, and filtered. The filtrate was vacuum distilled to yield 347 parts of 5-chloro-4-fluoro-2-nitrobenzotrifluoride.

(B) About 14 parts per hour of 5-chloro-4-fluoro-2-nitrobenzotrifluoride vapors and about 12 parts per hour of chlorine gas were passed simultaneously through a vapor phase reactor maintained at a temperature of about 320° to 380°. The vaporized reaction product was condensed and collected until about 14.7 parts of 5-chloro-4-fluoro-2-nitrobenzotrifluoride had been added and 14.7 parts of 2,5-dichloro-4-fluorobenzotrifluoride product was collected. The structure of the product was confirmed by gas chromatography—mass spectrum, $F^{19}$ and $C^{13}$ nuclear magnetic resonance analysis.

(C) Following the general procedure of Example II, the 2,5-dichloro-4-difluorobenzotrifluoride is reacted with potassium valinate to prepare 2-(2,5-dichloro-4-trifluoromethylphenylamino)-3-methylbutanoic acid.

EXAMPLE XII

A mixture of 15 parts of R-valine; 3218 parts of 3-chloro-4-fluorobenzotrifluoride; 5.3 parts of 4-chloro-3-fluorobenzotrifluoride; 17.9 parts of potassium carbonate; and 57.8 parts of N-methylpyrrolidinone was heated and maintained at about 140°–150° C., under a nitrogen atmosphere, for about 10 hours. The reaction mixture was allowed to cool to room temperature. The water, unreacted aromatic components and 47% of the N-methyl-pyrrolidinone were removed by vacuum distillation at 50 torrs and 55°–118° C. The reaction product was then further treated by alternate additions of hexane/toluene solvent and with water, then acidified by addition of about 25 parts of concentrated hydrochloric acid (37.9%) and the aqueous layer removed. The remaining organic layer was washed twice with water, dried over anhydrous sodium sulfate and the solvent removed under vacuum to yield 39.7 parts of a viscous oil. Analysis of the product by gas chromatographic techniques, using an internal standard, indicated 82.2% (32.6 parts) of R-2-(2-chloro-4-trifluoromethylphenylamino)-3-methyl butanoic acid—a yield of about 85.5% based on valine starting material.

What is claimed is:

1. A process for the preparation of anilino acids of the formula

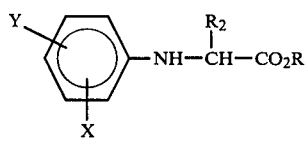

where R is H or a metal cation; $R_2$ is H or alkyl of 1 to 5 carbon atoms, lower alkenyl of 2 to 5 carbon atoms, lower haloalkyl of 1–4 carbon atoms, lower haloalkenyl of 2 to 4 carbon atoms, or lower cycloalkyl of 3 or 4 carbon atoms, Y is hydrogen, chloro, methyl group or trifluoromethyl group, and X is hydrogen chloro, or fluoro, which comprises reacting an aryl halide of the formula

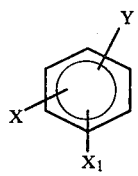

wherein $X^1$ is chloro or fluoro and X and Y are as defined above with the proviso that when $X^1$ is chloro, X is hydrogen or chloro, and when X and Y are both chloro, $X^1$ is fluoro, with an α-amino acid compound of the formula

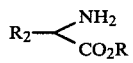

wherein R and $R_2$ are as defined above.

2. A process according to claim 1 carried out in the present of a dipolar aprotic solvent.

3. A process according to claim 2 wherein R is an alkali metal cation.

4. A process according to claim 2 wherein $R_2$ is lower alkyl of 2 to 5 carbon atoms.

5. A process according to claim 3 wherein the α-amino acid compound is an alkali metal salt formed in-situ by the reaction of an α-amino acid and an alkali metal compound.

6. A process according to claim 5 wherein the alkali metal compound is potassium carbonate.

7. A process according to claim 5 wherein $R_2$ is lower alkyl of 2 to 5 carbon atoms.

8. A process according to claim 7 wherein Y is $CF_3$.

9. A process according to claim 8 wherein the aryl halide is p-fluorobenzotrifluoride.

10. A process according to claim 8 wherein the aryl halide is p-chloro-benzotrifluoride.

11. A process according to claim 8 wherein the aryl halide is 3,4-dichlorobenzotrifluoride.

12. A process according to claim 8 wherein the aryl halide is 3,4-difluorobenzotrifluoride.

13. A process according to claim 8 wherein the aryl halide is 3-chloro-4-fluorobenzotrifluoride.

14. A process according to claim 8 wherein the aryl halide is 2-chloro-5-fluorobenzotrifluoride.

15. A process according to claim 8 wherein the aryl halide is 5-chloro-2-fluorobenzotrifluoride.

16. A process according to claim 8 wherein the aryl halide is 2,5-dichloro-4-fluorobenzotrifluoride.

17. A process according to claims 9, 10, 11, 12, 13, 14, 15, or 16 wherein the α-amino acid compound is potassium valinate.

18. A process for the preparation of isovaleric acid derivatives of the formula

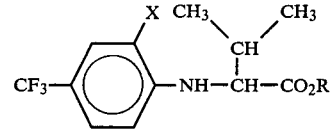

where R is hydrogen or a metal cation and X is hydrogen, fluoro or chloro, which comprises reacting a 4-halobenzotrifluoride is selected 4-chlorobenzotrifluoride; 4-fluorobenzotrifluoride; 3,4-dichlorobenzotrifluoride; 3,4-difluorobenzotrifluoride; and 3-chloro-4-fluorobenzotrifluoride with a metal valinate in the presence of a dipolar aprotic solvent.

19. A process according to claim 18 wherein the metal valinate is an alkali metal valinate.

20. A process according to claim 19 wherein the alkali metal is potassium.

21. A process according to claim 18 wherein the metal valinate is formed in-situ from the reaction of valine and an alkali metal carbonate.

22. A process according to claim 21 wherein the alkali metal carbonate is potassium carbonate.

23. A process according to claim 22 wherein potassium carbonate is present in an amount of at least about 0.5 moles in excess of the amount required to form potassium valinate in-situ.

24. A process according to claim 18 or 23 wherein the 4-halobenzotrifluoride is 4-chlorobenzotrifluoride.

25. A process according to claim 18 and 23 wherein the 4-halobenzotrifluoride is 4-fluorobenzotrifluoride.

26. A process according to claims 18 and 23 wherein the 4-halobenzotrifluoride is 3,4-dichlorobenzotrifluoride.

27. A process according to claims 18 and 23 wherein the 4-halobenzotrifluoride is 3,4-difluorobenzotrifluoride.

28. A process according to claim 18 and 23 wherein the 4-halobenzotrifluoride is 3-chloro-4-fluorobenzotrifluoride.

29. A process for the preparation of a potassium salt of R-2-(2-chloro-4-trifluoromethylphenylamino)-3-methylbutanoic acid which comprises reacting 3-chloro-4-fluorobenzotrifluoride with the R enantiomer of potassium valinate in a dipolar aprotic solvent at a temperature of about 110° to about 130° Celsius and in the presence of about 0.5 to about 0.75 moles of potassium carbonate in excess of the stoichiometric amount required to form potassium valinate.

30. A process for the preparation of R-2-(2-chloro-4-trifluoromethylphenylamino)-3-methylbutanoic acid which comprises reacting 3-chloro-4-fluorobenzotrifluoride with the R enantiomer of potassium valinate in a dipolar aprotic solvent at a temperature of about 110° to about 150° Celsius and in the presence of about 40 to about 75 mole percent of potassium carbonate in excess of the stoichiometric amount required to form potassium valinate and neutralizing to form the acid.

* * * * *